(12) United States Patent
Stamberg

(10) Patent No.: US 6,746,424 B2
(45) Date of Patent: Jun. 8, 2004

(54) SHAFTLESS BALLOON

(75) Inventor: Barbara E. Stamberg, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/460,185

(22) Filed: Dec. 11, 1999

(65) Prior Publication Data

US 2003/0139760 A1 Jul. 24, 2003

(51) Int. Cl.⁷ .............................................. A61M 29/00
(52) U.S. Cl. ................. 604/103.06; 604/96.01
(58) Field of Search .................. 604/103, 96.01, 604/102.02, 102.03, 103.07, 103.11, 103.12, 264; 606/194

(56) References Cited

U.S. PATENT DOCUMENTS

| | | | |
|---|---|---|---|
| 3,452,756 A | 7/1969 | Harautuneian | 264/264 |
| 3,544,668 A * | 12/1970 | Dereniuk | 264/135 |
| 4,083,369 A | 4/1978 | Sinnreich | 604/103.06 |
| 4,976,690 A * | 12/1990 | Solar et al. | 604/103.06 |
| 4,979,690 A | 12/1990 | Kita | 242/533.1 |
| 5,267,959 A * | 12/1993 | Forman | 604/103 |
| 5,306,246 A | 4/1994 | Sahatjian et al. | 264/515 |
| 5,769,817 A | 6/1998 | Burgmeier | 604/103.06 |
| 5,795,332 A * | 8/1998 | Lucas et al. | 604/103.06 |
| 6,132,824 A | 10/2000 | Hamlin | 428/35.2 |
| 6,221,043 B1 | 4/2001 | Fischell et al. | 604/103.06 |

* cited by examiner

Primary Examiner—Brian L. Casler
Assistant Examiner—Kevin C. Sirmons
(74) Attorney, Agent, or Firm—Fulwider Patton Lee & Utecht, LLP

(57) ABSTRACT

The invention is directed to a catheter assembly and the method for forming the same. The catheter includes an elongated shaft having proximal and distal sections, and further includes an inflatable balloon on a portion of the distal shaft section and in surrounding relation thereto. The balloon has proximal and distal tapered regions and an intermediate region longitudinally disposed therebetween. The proximal and distal tapered regions each has a first end adjacent the intermediate region and a second end opposite the first end. The wall thickness of the proximal and distal tapered regions, may, increase from the first end to the second end. A fluid-tight bond is formed between the catheter shaft and at least a section of at least one of the proximal and distal tapered regions at the second end thereof. The bond is preferably a fusion bond. At least a portion of the either or both the proximal and distal tapered regions in the bond interface is at least partially crystalline. Preferably, the crystallinity at the interface is greater than the crystallinity of the starting material from which the balloon is formed.

5 Claims, 5 Drawing Sheets

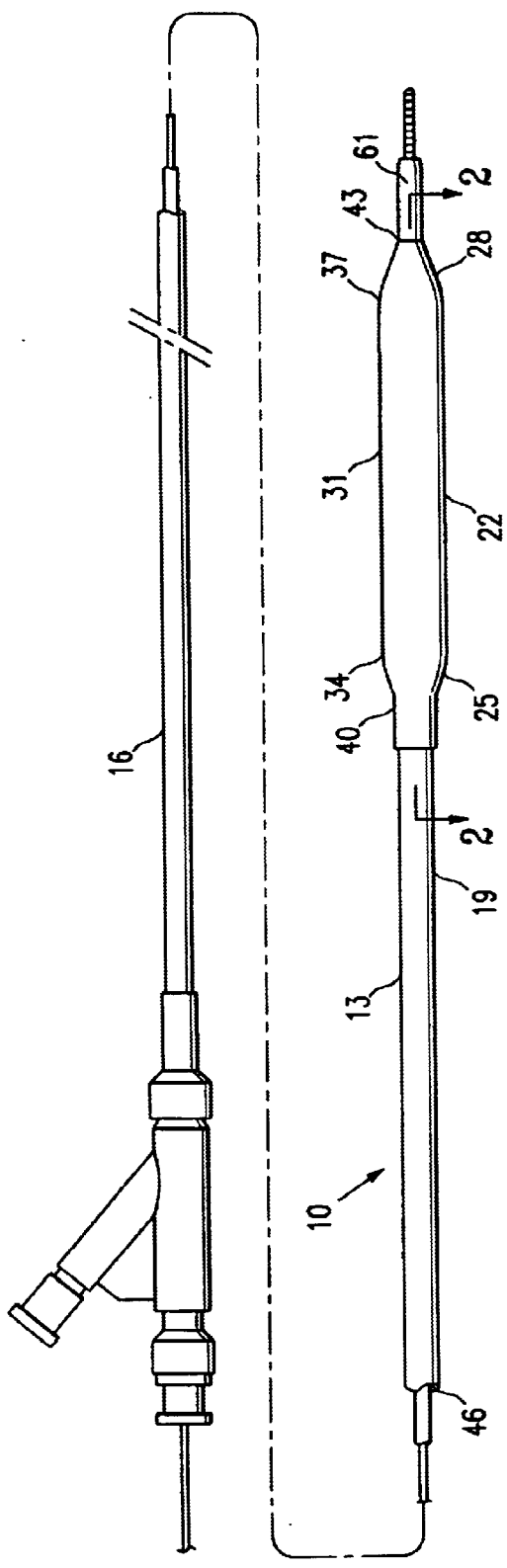
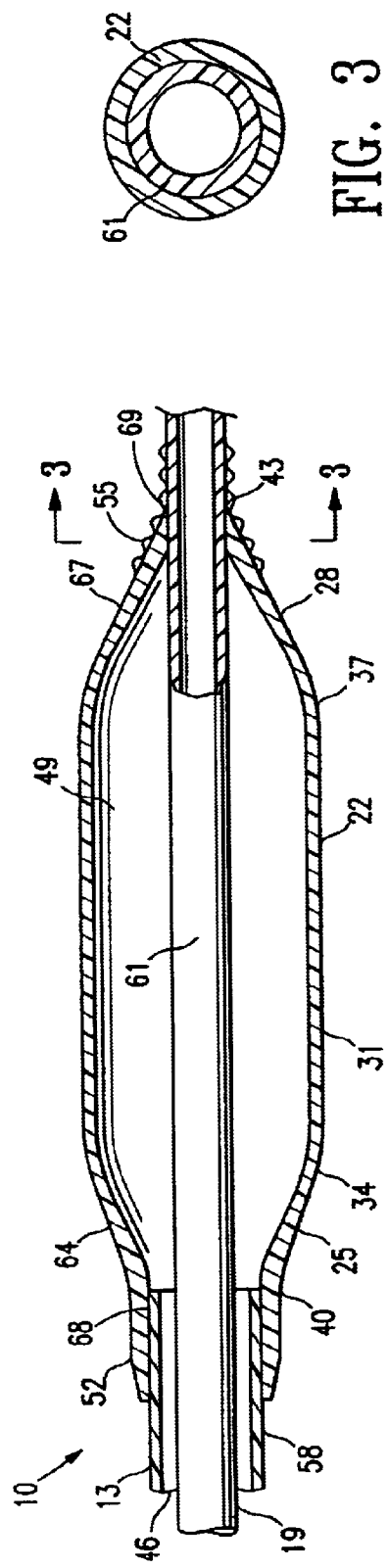
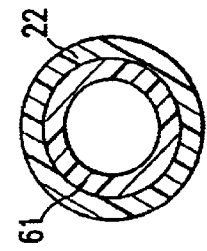
FIG. 1
FIG. 2
FIG. 3

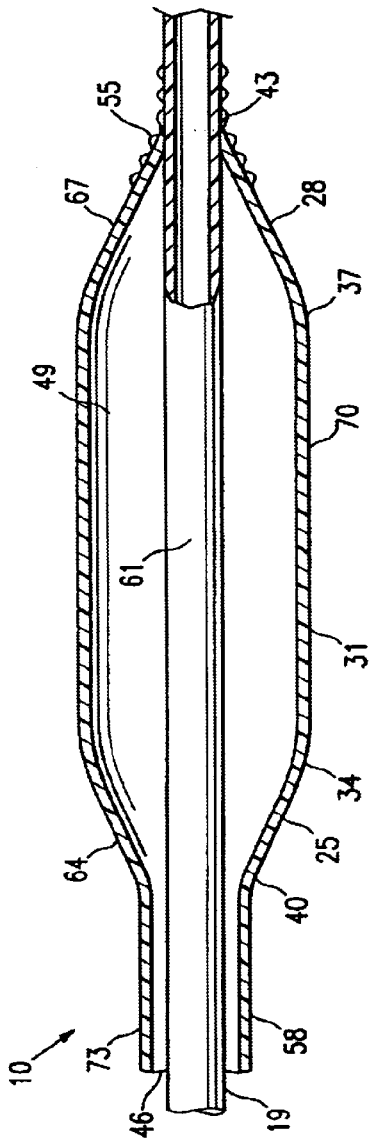
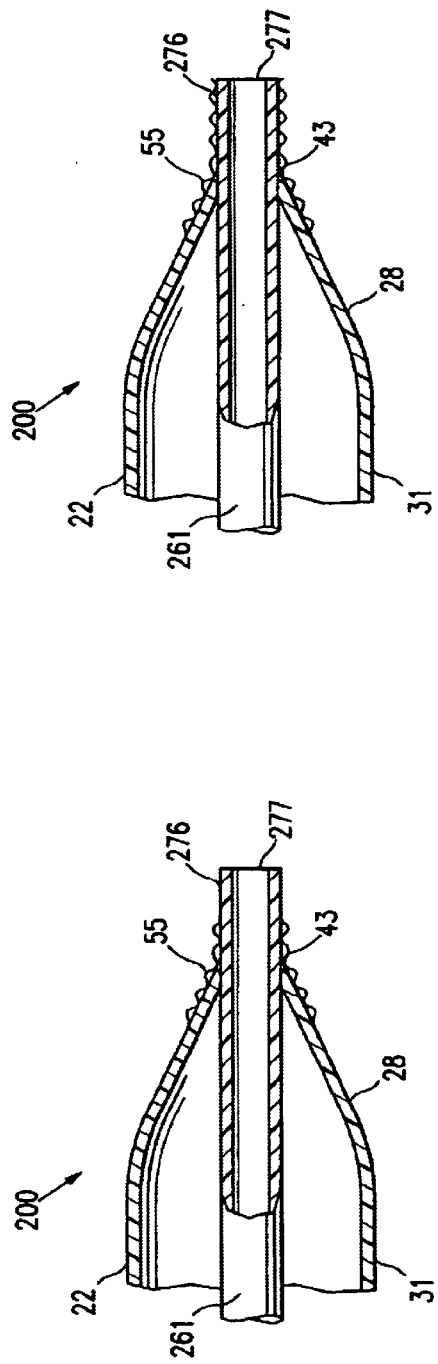
FIG. 4
FIG. 5A
FIG. 5B

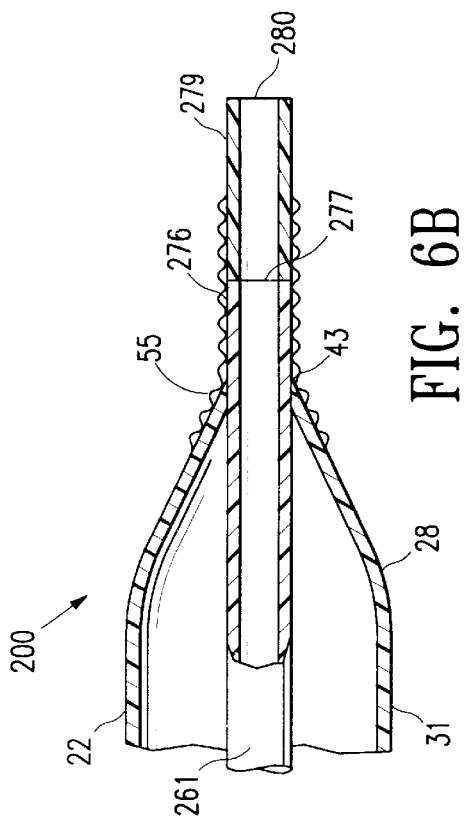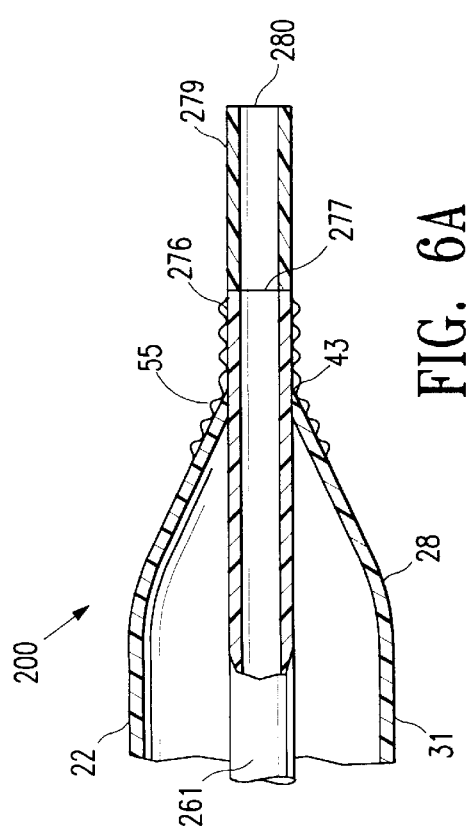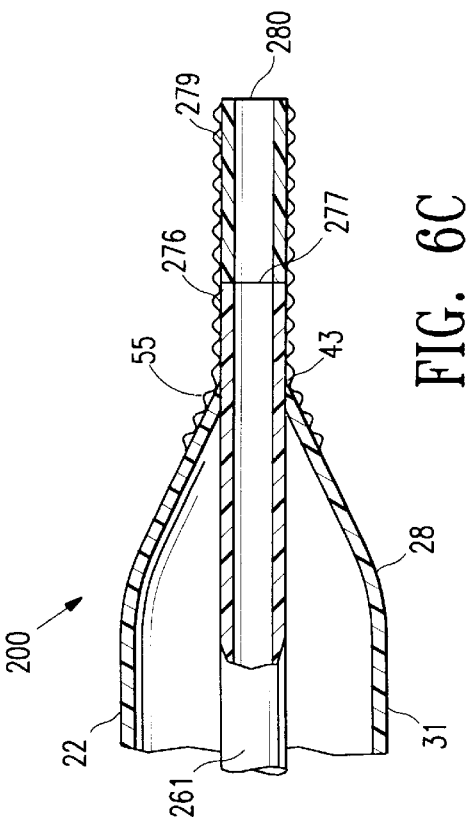
FIG. 6A
FIG. 6B
FIG. 6C

SHAFTLESS BALLOON

FIELD OF INVENTION

The invention relates to the field of intravascular delivery systems, and more particularly to dilatation balloon catheters.

BACKGROUND OF THE INVENTION

In percutaneous transluminal coronary angioplasty (PTCA) procedures, a guiding catheter is advanced until the distal tip of the guiding catheter is seated in the ostium of a desired coronary artery. A guide wire, positioned within an inner lumen of an dilatation catheter, is first advanced out of the distal end of the guiding catheter into the patient's coronary artery until the distal end of the guide wire crosses a lesion to be dilated. Then the dilatation catheter having an inflatable balloon on the distal portion thereof is advanced into the patient's coronary anatomy, over the previously introduced guide wire, until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion.

In the design of catheter balloons, balloon characteristics such as strength, flexibility and compliance must be tailored to provide optimal performance for a particular application. An important consideration in the design of the dilatation catheter assemblies is the flexibility of the distal tip of the catheter at the distal end of the balloon while maintaining the strength of the bond between the catheter and the balloon material. This flexibility affects the ability of the catheter for negotiating through the patient's vasculature without causing injury thereto.

Therefore, what has been needed is a dilatation balloon catheter with a flexible tip and while maintaining the integrity of the bond between the catheter and the balloon. The present invention satisfies these and other needs.

SUMMARY OF THE INVENTION

The invention is directed to a catheter assembly. The catheter includes an elongated shaft having proximal and distal sections, and further includes an inflatable balloon on a portion of the distal shaft section and in surrounding relation thereto. The balloon has proximal and distal tapered regions and an intermediate region longitudinally disposed therebetween. The proximal and distal tapered regions each has a first end adjacent the intermediate region and a second end opposite the first end. The wall thickness of the proximal and distal tapered regions, may, increase from the first end to the second end. A fluid-tight bond is formed between the catheter shaft and at least a section of at least one of the proximal and distal tapered regions at the second end thereof. The bond is preferably a fusion bond. At least a portion of the either or both the proximal and distal tapered regions in the bond interface is at least partially crystalline. Preferably, the crystallinity at the interface is greater than the crystallinity of the starting material from which the balloon is formed.

In an alternate embodiment, the assembly further includes an atraumatic distal tip with a distal end disposed at least substantially coaxial with the distal shaft section and extends distally from the second end of the balloon. A bond is formed between the catheter shaft and the second end of the balloon.

In another embodiment, a cylindrical collar is disposed at least partially about the atraumatic distal tip and at least partially about tip portion of the distal catheter shaft. The collar forms a distal bond with at least a section of the distal tapered region at the second end thereof.

The balloon, atraumatic distal tip, and the collar are formed, at least in part, from a material independently selected from the group consisting of copolyamides, polyurethane, and copolyesters.

The invention is also directed to a method for forming the catheter assembly of the present invention. By way of manufacture, an elongated shaft having proximal and distal sections and a distal tip is provided. An inflatable balloon is disposed on a portion of the distal shaft section in surrounding relation thereto. The balloon has proximal and distal tapered regions and a intermediate region longitudinally disposed therebetween. The proximal and distal tapered regions each has a first end adjacent the intermediate region and a second end opposite the first end. Furthermore, the balloon has proximal and distal shaft regions adjacent the second end of the proximal and distal tapered regions, respectively. The proximal and distal shaft regions extend away from the first end of the corresponding proximal and distal tapered regions.

The balloon distal shaft region at the second end of the distal tapered region is removed such that the balloon material at least substantially terminates at the second end of the tapered region. A protective sleeve is provided at the balloon distal tapered region. The protective sleeve covers, at least in part, the second end of the balloon tapered region and the shaft distal tip.

A substantially monochromatic energy at a wave length of maximum spectral absorption of the materials forming the balloon and the distal section of the catheter shaft is controllably directed onto the distal catheter shaft and at least a section of the distal tapered region at the second end thereof to concentrate the monochromatic energy to form a bond site between the distal catheter shaft and the at least a section of the distal tapered region. At least a portion of the materials forming the distal catheter shaft and the balloon along the bond site and the region immediately adjacent thereto is melted. The melted material is then allowed to cool and solidify to form a fusion bond between the distal catheter shaft and the balloon. The protective sleeve is then removed.

BRIEF DESCRIPTION OF THE DRAWINGS

FIG. 1 is an elevational view of a balloon catheter embodying features of the invention.

FIG. 2 is a longitudinal cross-sectional view of the catheter shown in FIG. 1 taken within lines 2—2.

FIG. 3 is a cross sectional view of the balloon catheter of FIG. 2 taken along lines 3—3.

FIG. 4 is a longitudinal cross-sectional view of an alternative embodiment of a balloon catheter which embodies features of the invention, the balloon and the outer tubular member being integral with one another.

FIG. 4 is an enlarged longitudinal cross-sectional view of one embodiment of the invention showing a fused interface between a coextruded balloon and distal catheter shaft.

FIGS. 5(A) and 5(B) are enlarged longitudinal cross-sectional views of other embodiments of the invention showing a fused interface between the balloon and distal catheter shaft with a bond formed along a portion of the distal tapered region of the balloon, the bond extending distally along a length of a tip portion of the catheter.

FIGS. 6(A), 6(B), and 6(C) are enlarged longitudinal cross-sectional views of other embodiments of the invention showing an atraumatic distal tip disposed adjacent the distal tip of the shaft showing a fused interface between the balloon and distal catheter shaft with a bond extending along a portion of the distal tapered region of the balloon, the bond extending distally along a length of the catheter tip or the atraumatic tip.

DETAILED DESCRIPTION OF THE INVENTION

Figure 7A:
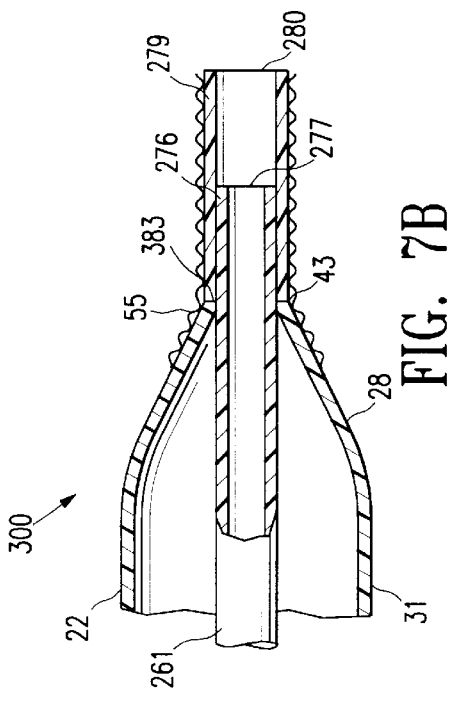
FIGS. 7(A) and 7(B) are enlarged longitudinal cross-sectional views of other embodiments of the invention showing a fused interface between the balloon and an atraumatic distal tip disposed at least substantially coaxial with the tip portion and in surrounding relation thereto. The distal bond extends distally along various portions of the atraumatic distal tip.

In the embodiment features of which are illustrated in FIG. 1, the catheter 10 of the present invention is a balloon catheter having an elongated catheter shaft 13 having a proximal section 16 and a distal section 19 with an inflatable balloon 22 on the distal section 19 of the shaft 13 and in surrounding relationship thereto. The balloon 22 has a proximal tapered region 25 and a distal tapered region 28 and an intermediate region 31 longitudinally disposed between the proximal and distal tapered regions 25 and 28.

The proximal and distal tapered regions 25 and 28 each has a first end 34 and 37, respectively, and a second end 40 and 43 opposite their respective first ends, 34 and 37. A shaft lumen 46 is in fluid communication with the balloon interior 49. A stent (not shown) may be mounted on at least a portion of the intermediate region 31 to form a stent delivery catheter system.

The balloon 22 is sealingly secured to the shaft 13 by one or more bonds, preferably, fusion bonds 52 and 55 (as shown in FIG. 2), at or near either or both the proximal and distal balloon second ends 40 and 43. The one or more bonds 52 and 55 are each formed at an interface between the shaft 13 and the balloon 22. The longitudinal dimension of bonds 52 and 55, as shown in some figures, such as FIG. 2, is for illustrative purposes only and is not necessarily meant as an exact graphical representation of the bonds' proportional length, unless otherwise stated.

In the embodiment features of which are illustrated in FIGS. 2 and 3, the catheter shaft 13 comprises an outer tubular member 58 and an inner tubular member 61. The balloon 22 is bonded, preferably fusion bonded, to the outer tubular member 58 by the proximal fusion bond 52, and to the inner tubular member 61 by the distal fusion bond 55.

The longitudinal dimension of the proximal and distal fusion bonds 52 and 55, independently, may range from about 0.25 to about 10 millimeters (mm), preferably, from about 1 to about 7 mm; depending on the presence and configuration of other components, as described in more detail below. The distal fusion bond 55 has a proximal longitudinal dimension extending along at least a portion of the distal tapered region 28 of the balloon 22 toward the intermediate region 31, and ranges from about 0.05 to about 1 mm; preferably from about 0.2 to about 0.3 mm. The tapered regions 25 and 28 each has a wall thickness 64 and 67 respectively, which may increase from their respective first ends, 34 and 37, to their respective second ends, 40 and 43.

In an alternative embodiment illustrated in FIG. 4, a coextruded balloon 70 and catheter shaft 73 is fusion bonded to the shaft inner tubular member 61 by the distal fusion bond 55.

FIGS. 5(A) through 9(B), wherein like reference indicate like features, illustrate features of different embodiments of the present invention. In FIGS. 5(A) and 5(B), a catheter assembly 200 has a distal shaft (not shown) with an inner tubular member 261, the distal shaft having a tip portion 276 with a distal end 277. The tip portion 276 of the distal shaft has a longitudinal dimension ranging from about 0.5 to about 3 mm, preferably from about 1 to about 3 mm. The distal fusion bond, may extend along a portion or all of the tip portion 276, as shown in FIGS. 5(A) and 5(B), respectively.

Optionally, as illustrated in FIGS. 6(A) and 6(B), the distal shaft has an atraumatic distal tip 279 with a distal end 280, and disposed distally adjacent the distal tip 276 in a butting relationship thereto. The distal bond 55 may extend along a portion (FIG. 5(A)) or all of the length of the tip portion 276 (FIG. 6(A)). Additionally, the distal bond 55 may extend distally along a portion or the entire length of the atraumatic tip 279, as shown in FIGS. 6(B), 6(C). The atraumatic distal tip 279, itself, has a longitudinal dimension in a range from about 2 to about 6 millimeter (mm).

Figure 7B:
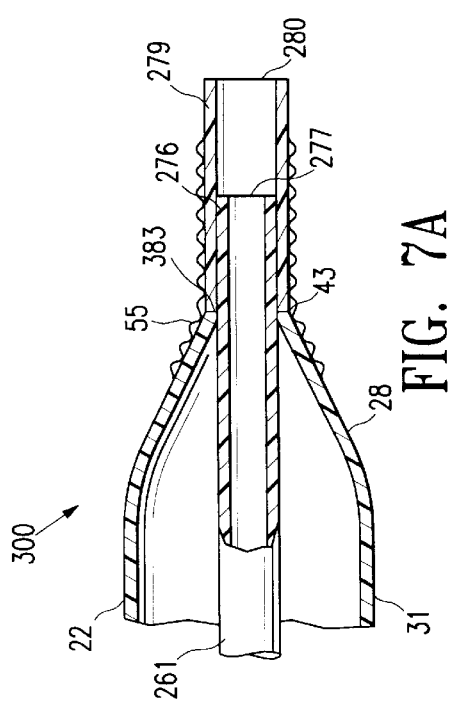

In FIGS. 7(A) and 7(B), in an alternative embodiment, a catheter assembly 300, the atraumatic distal tip 279 is disposed at least substantially coaxial with the tip portion 276 and is in surrounding relation thereto. The atraumatic tip 279 at its proximal end has an interface 383 with the distal end 43 of the balloon 22. The distal bond 55 may extend along the longitudinal dimension of the atraumatic tip 279 to a point distal to the distal end 277 of the tip 276, as shown in FIG. 7(A), or along the entire longitudinal dimension of the atraumatic tip 379, as shown in FIG. 7(B), or somewhere in between.

Figure 8A:
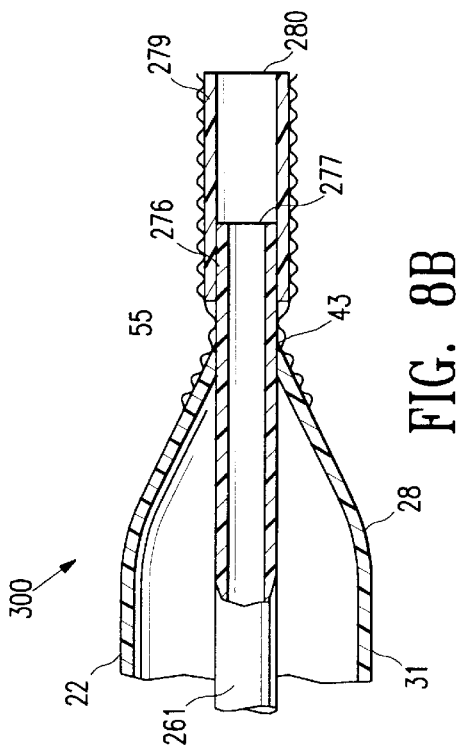
FIGS. 8(A) and 8(B) are enlarged longitudinal cross-sectional views of other embodiments of the invention showing the atraumatic tip being spaced apart from a second end of the balloon. The distal bond extends distally along various portions of the atraumatic distal tip.
Figure 8B:
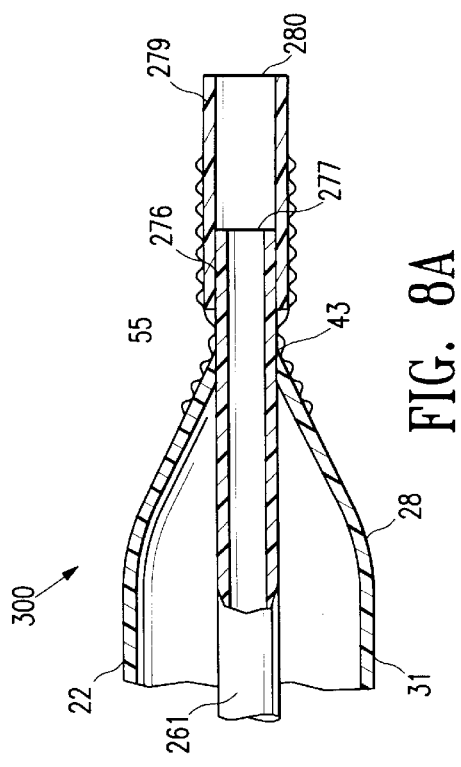

The atraumatic tip 279 may form a distal fusion bond 55 with at least a section of the distal tapered region 28, as illustrated in FIGS. 7(A) and 7(B)). Alternatively, as illustrated in FIGS. 8(A) and 8(B), the atraumatic tip 279 may be spaced apart from the second end 43 of the balloon 22. The distal bond 55 may extend along the longitudinal dimension of the atraumatic tip 279 to a point distal to the distal end 277 of the tip 276, as shown in FIG. 8(A), or along the entire longitudinal dimension of the atraumatic tip 279 to the distal end 280, as shown in FIG. 8(B), or somewhere in between.

Figure 9A:
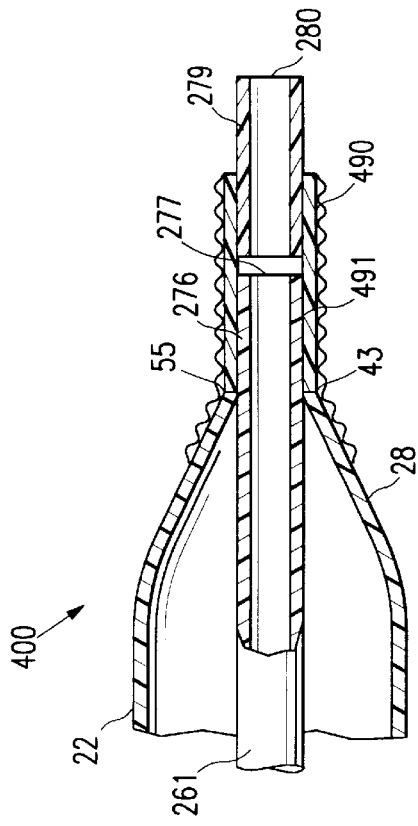
FIGS. 9(A) and 9(B) are enlarged longitudinal cross-sectional views of other embodiments of the invention showing a cylindrical collar disposed at least partially about the atraumatic tip and at least partially about the tip portion of the distal shaft catheter. The distal bond extends distally along various portions of the collar.

In an alternate embodiment, features of which are illustrated in FIG. 9(A), the assembly 400 further includes a cylindrical collar 490 disposed at least partially about the atraumatic tip 379 and at least partially about the tip portion 276 of the distal shaft catheter. The collar 490 has an interface 491 with the distal end 43 of the balloon 22 and forms the fluid-tight distal bond 55 with at least a section of the distal tapered region 28 at the second end 43 thereof. The distal bond 55 may extend along the entire longitudinal dimension of the collar 490 as shown in FIG. 9(A), or additionally, may extend distally to the distal end 280 of the atraumatic tip 279.

Figure 9B:
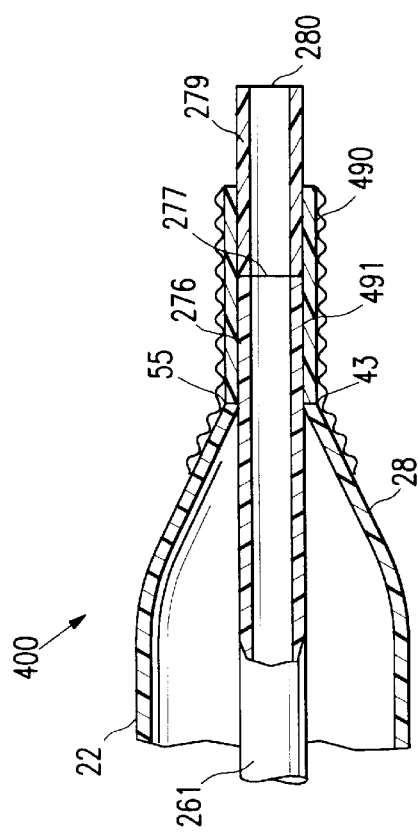

In an alternate embodiment, features of which are illustrated in FIG. 9(B), the atraumatic distal tip 279 is spaced apart from the tip 276.

The balloon 22, the atraumatic tip 279, and the collar 490 may be formed of a thermoplastic elastomer (TPE) with various properties. The preferred balloons of the invention are made of polyamide/polyether block copolymers. The polyamide/polyether block copolymers are commonly identified by the acronym PEBA (polyether block amide). The polyamide and polyether segments of these block copolymers may be linked through amide linkages, however, most preferred are ester linked segmented polymers, i.e. polyamide/polyether polyesters. Such polyamide/polyether/ polyester block copolymers are made by a molten state polycondensation reaction of a dicarboxylic polyamide and a polyether diol. The result is a short chain polyester made up of blocks of polyamide and polyether. The polyamide and polyether blocks are not miscible. Thus the materials are characterized by a two phase structure: one is a thermoplastic region that is primarily polyamide and the other is elastomer region that is rich in polyether. The polyamide segments are semicrystalline at room temperature. The generalized chemical formula for these polyester polymers may be represented by the following formula:

in which PA is a polyamide segment, PE is a polyether segment and the repeating number n is between 5 and 10. The polyamide/polyether polyesters are sold commercially under the PEBAX® trademark by companies such as Elf Atochem North America Inc. of Philadelphia, Pa. Examples of suitable commercially available polymers are Pebax® 33 series polymers. The suitable material for the balloon, atraumatic tip, and collar preferably have different hardness values and are selected to provide the necessary flexibility. For example, the balloon material may be selected from material with hardness 60 and above, Shore D scale, more preferably, Pebax® 7033 and 7233.

The inner tubular member of the shaft may be formed of any suitable material compatible with the material to which it will be fusion bonded. For example, the inner tubular member may be a multilayer tubular member with a first or outer layer which is fusion bondable to one or more of the materials for forming the balloon, atraumatic tip, and cylindrical collar; and a second or inner layer which has lubricious properties. A high strength outer layer may be bonded to at least part of the first layer to provide additional strength and pushability. The first layer should have a melting point which is at least 20° C., preferably at least 30° C. lower than the melting point of an adjacent polymeric layer, so that the adjacent layer is not distorted by the heat from the fusion bonding procedure.

The material from which the first layer of the multilayered member, which has a lower melting point than the adjacent second layer, is selected so as to be compatible with the polymeric material of the catheter component to which it is to be secured (e.g., balloon, atraumatic tip, and cylindrical collar). A presently preferred lower melting point polymeric material is a polyolefin based copolymer with not more than 35% (by weight) reactive monomer forming the copolymer. A suitable polyolefin material is copolymerized with one or more monomers selected from the group consisting of carboxylic acid or acrylic acid or anhydride thereof and preferably is unsaturated. A presently preferred polyolefinic material is a polyethylene based adhesive polymer such as ethylene-acrylic acid copolymer which is sold commercially as PRIMACOR by Dow Chemical Co. or as ESCOR by EXXON or as PLEXAR by Quantum Chemical Corp. Other suitable materials include polymers which have been modified by reactive extrusion having a durometer range of about Shore A 80 to about Shore D 80, preferably about Shore A 90 to about Shore D 70.

The second or inner layer of the multilayer member having lubricious properties should have a coefficient of friction (both static and dynamic) of less than 0.35 and preferably less than 0.30. Suitable polymeric materials having the aforesaid coefficient of friction include polyethylene, polytetrafluoroethylene and other fluoropolymers.

A third layer may be provided on the side of the first layer opposite side in contact with the second layer and may be formed of various polymeric materials to provide a catheter shaft with additional push and to prevent collapse or kinking of the tubular member in manufacturing or use. Suitable polymeric materials for the third layer include high density polyethylene, polyethylene terephthalate (PET), polyamide, a thermoplastic polyurethane, polyetheretherketone (PEEK) and the like.

All or most of the layers of the multilayered tubular member are preferably selected or modified so that they can be melt processed, e.g. coextruded, simultaneously or sequentially, and as a result the polymeric materials of the various layers should be compatible in this regard or made compatible by appropriate additives to the polymers.

By way of forming the catheter assembly of the present invention, such as catheter assembly 300, the distal shaft (not shown) of the balloon is first removed at the second end 43 of the distal tapered region 28 such that the balloon material at least substantially terminates at the second end 43. Substantially monochromatic energy at a wavelength of maximum spectral absorption of the materials forming the balloon and the distal section of the catheter shaft is applied to the desired interface to be bonded (e.g., interface between the second end 43 of the balloon and the proximal end of the distal tip of the catheter shaft, the proximal end of the atraumatic tip, or the proximal end of the collar). The monochromatic energy is controllably directed onto the desired interface to concentrate the monochromatic energy to form a bond site between the distal catheter shaft and the at least a section of the distal tapered region. The materials forming the distal catheter shaft and the balloon along the bond site and the immediate region thereof are then melted; followed by allowing the previously melted materials to cool and solidify to form a fusion bond between the distal catheter shaft and the balloon and any other necessary parts. The interface between the balloon material and the one or more components, such as the tip 276, atraumatic tip 279, and collar 490; may, preferably, have a crystallinity greater than the crystallinity of the starting material.

Figure 10:
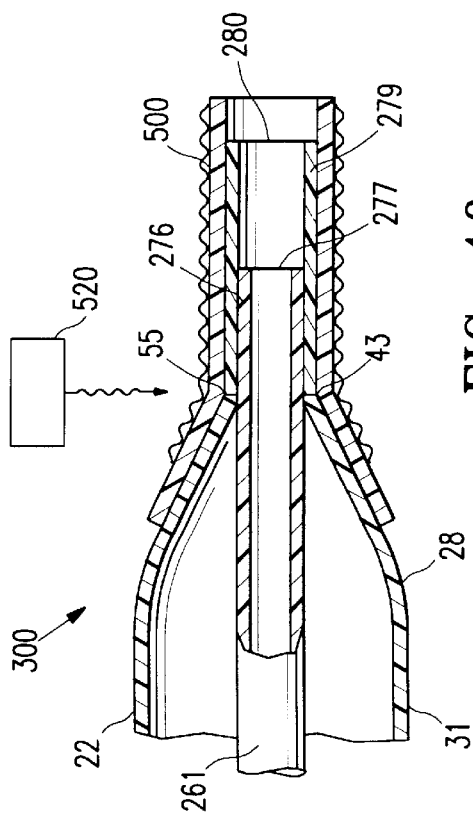
FIG. 10 is an enlarged longitudinal cross-sectional view of one embodiment of the invention showing a shrink tubing placed around distal tapered portion of the balloon, distal tip of the distal shaft, and the atraumatic tip with the desired area being heated to induce shrinking and forming a tight fit between the surfaces.

As illustrated in FIG. 10, in the method of forming the balloon catheter 300 (see FIG. 7) of the invention, a shrink tubing 500 is placed around the distal tapered portion 28 of the balloon 22, distal tip 276 of the distal shaft (not shown), and the atraumatic tip 379, and the desired area is heated to induce shrinking and to form a tight fit between the surfaces to be bonded (e.g., balloon, distal tip of the shaft and the atraumatic tip). Heat sufficient to melt the substrates is controllingly directed from a heat source 520 to the catheter assembly 300 to be bonded. The presently preferred fusion heat source is a $CO_2$ laser. The laser power is about 50 mW to about 250 mW, the laser rotation speed about the members to be bonded is about 75 to about 300, and the laser absolute focus is about 0.30 to about 0.50. The materials are heated at temperatures between about 100° C. to about 200° C. for about 30 to about 150 seconds. The melted substrates are then allowed to cool down and fuse together into a fusion bond, with the shrink tubing 500 removed thereafter.

While particular forms of the invention have been illustrated and described, it will be apparent that various modifications can be made without departing from the spirit and scope of the invention. Accordingly, it is not intended that the invention be limited, except as by the appended claims.

What is claimed is:

1. A balloon catheter, comprising:

an elongated shaft comprising an outer tubular member and an inner tubular member, and having proximal and distal sections;

an inflatable balloon on a portion of the distal shaft section and in surrounding relationship to the portion of the distal shaft section, the balloon having proximal and distal tapered regions and an intermediate region longitudinally disposed therebetween, the proximal and distal tapered regions each having a first end adjacent the intermediate region and a second end opposite the first end and a wall thickness increasing from the first end to the second end; and a proximal fluid-tight bond between the catheter shaft outer tubular member and at least a section of the proximal tapered region so that the wall thickness of the section of the proximal tapered region bonded to the catheter shaft outer tubular member increases along the length of the bond, and a distal fluid-tight bond between the catheter shaft inner tubular member and at least a section of the distal tapered region, so that the wall thickness of the section of the distal tapered region bonded to the catheter shaft inner tubular member increases along the length of the bond.

2. The balloon catheter of claim 1 wherein the proximal fluid-tight bond has a longitudinal dimension which is about 0.05 to about 1 mm, and the distal fluid-tight bond has a longitudinal dimension which is about 0.5 to about 1 mm.

3. The balloon catheter of claim 2 wherein the longitudinal dimension of the proximal fluid-tight bond is about 0.2 to about 0.3 mm, and the longitudinal dimension of the distal fluid-tight bond is about 0.2 to about 0.3 mm.

4. A balloon catheter, comprising:

an elongated shaft comprising an outer tubular member and an inner tubular member, and having proximal and distal sections;

an inflatable balloon on a portion of the distal shaft section and in surrounding relationship to the portion of the distal shaft section, the balloon having proximal and distal tapered regions and an intermediate region longitudinally disposed therebetween, the proximal and distal tapered regions each having a first end adjacent the intermediate region and a second end opposite the first end and a wall thickness increasing from the first end to the second end; and a proximal fluid-tight bond between the catheter shaft outer tubular member and at least a section of the proximal tapered region, so that the wall thickness of the section of the proximal tapered region bonded to the catheter shaft outer tubular member increases along the length of the bond, and a distal fluid-tight bond between the catheter shaft inner tubular member and at least a section of the distal tapered region, so that the wall thickness of the section of the distal tapered region bonded to the catheter shaft inner tubular member increases along the length of the bond, said section of the proximal tapered region and said section of the distal tapered region having at least a partial crystalline composition.

5. The balloon catheter of claim 4 wherein said section of the proximal tapered region and said section of the distal tapered region have a crystallinity greater than that of a starting material forming said sections of the proximal and distal tapered regions.

* * * * *

UNITED STATES PATENT AND TRADEMARK OFFICE
CERTIFICATE OF CORRECTION

PATENT NO. : 6,746,424 B2
DATED : June 8, 2004
INVENTOR(S) : Barbara E. Stamberg It is certified that error appears in the above-identified patent and that said Letters Patent is hereby corrected as shown below:

Title page,
Item [56], References Cited, U.S. PATENT DOCUMENTS, insert the following:

| -- 4,261,339 A | 4/1981 | Hanson | 128/1 D |
| 4,346,698 A | 8/1982 | Hanson | 128/1 D |
| 5,041,125 A | 8/1991 | Montano | 606/192 |
| 5,087,246 A | 2/1992 | Smith | 604/96 |
| 5,334,146 A | 8/1984 | Ozasa | 604/96 |
| 5,423,854 A | 6/1995 | Cornelius | 604/103 |
| 5,549,552 A | 8/1996 | Peters | 604/96 |
| 5,643,209 A | 7/1997 | Fugoso | 604/96 |
| 5,853,389 A | 12/1998 | Hijlkema | 604/96 --. |

Signed and Sealed this

Fourth Day of January, 2005

JON W. DUDAS
*Director of the United States Patent and Trademark Office*